US011432485B2

(12) United States Patent
Larsen

(10) Patent No.: US 11,432,485 B2
(45) Date of Patent: Sep. 6, 2022

(54) ARTIFICIALLY INTELLIGENT IRRIGATION SYSTEM

(71) Applicant: Smart Rain Systems, LLC, Centerville, UT (US)

(72) Inventor: Rudy Lars Larsen, Bountiful, UT (US)

(73) Assignee: Smart Rain Systems, LLC, Centerville, UT (US)

( * ) Notice: Subject to any disclaimer, the term of this patent is extended or adjusted under 35 U.S.C. 154(b) by 281 days.

(21) Appl. No.: 16/884,907

(22) Filed: May 27, 2020

(65) Prior Publication Data

US 2020/0383284 A1 Dec. 10, 2020

Related U.S. Application Data

(60) Provisional application No. 62/859,517, filed on Jun. 10, 2019.

(51) Int. Cl.
*A01G 25/16* (2006.01)
*G01W 1/14* (2006.01)
*G01W 1/10* (2006.01)

(52) U.S. Cl.
CPC ............. *A01G 25/167* (2013.01); *G01W 1/10* (2013.01); *G01W 1/14* (2013.01)

(58) Field of Classification Search
CPC ........ A01G 25/167; G01W 1/10; G01W 1/14; G01N 33/246; G06Q 50/02
See application file for complete search history.

(56) References Cited

U.S. PATENT DOCUMENTS

| 10,772,269 B2* | 9/2020 | Fleming | G06Q 50/02 |
| 2008/0157990 A1* | 7/2008 | Belzer | G06Q 10/087 |
| | | | 340/678 |
| 2016/0073573 A1* | 3/2016 | Ethington | G06Q 50/02 |
| | | | 705/7.36 |
| 2016/0078375 A1* | 3/2016 | Ethington | G06Q 10/04 |
| | | | 705/7.27 |

(Continued)

OTHER PUBLICATIONS

Babazadeh et al. ,Highly-Distributed Sensor Processing using IoT for Critical Infrastructure Monitoring, IEEE 2017 (Year: 2017).*

(Continued)

*Primary Examiner* — Mohammad K Islam
(74) *Attorney, Agent, or Firm* — Dentons Durham Jones Pinegar; Sarah W. Matthews; James Larson

(57) ABSTRACT

An artificially intelligent irrigation system on a property may include an irrigation management server with the information for the irrigation system. An artificial intelligence feature may retrieve and access inputs from a plurality of resources or data sources. These sources may include current weather data, historical weather data, current moisture levels, historical moisture levels, sensor information from sensors on or near the property, water utility usage data, and other data. Other inputs may be events on the property as well the frequently or consistently occur and may also be considered historical data. The artificial intelligence feature may manage the schedule and predict the upcoming water schedule based on this information and appropriately water, or not water, or change duration of watering or output of watering based on the information gathered without human intervention.

17 Claims, 11 Drawing Sheets

(56) References Cited

U.S. PATENT DOCUMENTS

2016/0147962 A1* 5/2016 Vollmar ............... H04W 4/029
 705/2
2016/0232621 A1* 8/2016 Ethington .............. G06Q 50/02

OTHER PUBLICATIONS

Wicki et al., Assessing the potential of soil moisture measurements for regional landslide early warning, 2020 (Year: 2020).*

* cited by examiner

ARTIFICIALLY INTELLIGENT IRRIGATION SYSTEM

This application claims priority to U.S. provisional application 62/859,517 (the '517 application) filed Jun. 10, 2019. The '517 application is hereby incorporated herein in its entirety.

FIELD

This disclosure relates generally to an irrigation system that assumes actions of a landscape owner and even more specifically an irrigation system that learns from sources within the irrigation system and outside the irrigation system to artificially manage the irrigation system without human interaction, or with minimized human interaction. The irrigation system may adjust, manage and implement the system using a plurality of resources.

RELATED ART

Controllers for irrigation systems have been utilized for decades to make it easier on property owners to water their landscapes. Simple systems for watering may include a start time and finish time for specific zones for a given landscape.

Smart controllers have become more and more common in the irrigation industry. Smart controllers and smart controller technology allows for a user to quickly and effectively make changes to an irrigation system, or system.

Commercial and residential systems are taking advantage of smart controllers and the use of sensors to more effectively manage water usage. Systems often have an easy way or method for a user to now interact with the irrigation systems by having an application (or app) on a phone that allows them to make changes to the system. Other computers or tablets may also be used to manipulate and control the system by relaying messages to the smart controllers which carry out the tasks.

Some smart controllers may even learn from the way people control them. For example, some smart thermostats have applied an individual rules-and-exceptions-based learning approach to automatically generate temperature setpoint schedules. The rules- and-exceptions-based learning approach may involve observing interactions with the smart thermostat over time and, based on certain defined rules and exceptions, determine whether the interactions have some meaning that should be used to build a temperature setpoint schedule. However, rules-and-exceptions-based learning may not be the most effective way to control an irrigation system, as users do not always set rules and schedules that reflect the most efficient watering schedule. For example, many users set their irrigation systems to water at a specific time every day, and neglect to change the schedule if precipitation occurs.

Additionally, there may be events other than precipitation that may affect soil moisture levels at the user's property after a lag time. For example, a watering event at a nearby property may affect soil moisture levels at the user's property after a lag time. Precipitation events at remote locations may also, after a given lag time, affect soil moisture levels at the user's property. Thus, setting a watering schedule to water only based on the current soil moisture level may not be the most efficient watering schedule. However, it is difficult to train a smart controller to water based on events that occur away from the user's property because it may be difficult to establish a ground truth soil moisture based on such events, needed to determine a soil moisture function that maps predictive soil moisture to the data from remote locations.

Thus, there is a need for a smart watering system that can generate a training data set to determine soil moisture functions that map predictive soil moisture to the data from remote locations. It may also be advantageous for the system to continuously monitor ground truth soil moisture to check the accuracy of the soil moisture function for the predictive soil moisture, and update a baseline watering schedule as a result of the predictive soil moisture.

SUMMARY

One aspect of the present disclosure is directed to an artificial intelligence system for predicting soil moisture and using the predictive soil moisture to manage watering of an irrigation system.

This disclosure, in at least one aspect, relates to irrigation systems, including utility and function of an irrigation system with minimal or no human involvement. More generally the disclosure relates to a system with inputs from within an irrigation system and outside the irrigation system to manage the watering and irrigation of a given property. The inputs within the irrigation system may include, for example, water flow measurements, soil moisture levels, etc. Inputs from outside the irrigation system may include, for example, third party weather service data for a location remote from the user's property, water flow measurements at a second property, and/or soil moisture levels at a second property, etc.

The system may provide several different solutions to watering of property or landscape. An artificial intelligence (AI) feature may be utilized to provide for a plurality of inputs to be made into the system to have the system run primarily or entirely on its own. Firstly, one portion of the method to allow the AI feature to function is the AI may auto-review prior adjustments to watering zones, program changes or creations based on historical data and adjusts schedules and times based on this data alone to create a baseline watering schedule.

Secondly, the AI may use local sensor data from an extended network of irrigation systems, including but not limited to moisture sensors, rain sensors, water flow sensors, and other water station sensors and gather local data within a given range (such as a 5 to 15 mile radius, but the range may have other suitable distances, shapes and sizes depending on the property). Based on this collected data by itself or in connection with the historical data, the AI may generate a training data set that determines a soil moisture function that maps predictive soil moisture to the collected data. Based on the predictive soil moisture, the AI may automatically make changes to the baseline water programs and/or zones.

Thirdly, information based on historical micro climate data, such as rain fall or other weather data, from other sites, or landscape sites, and how it may impact surrounding sites may be collected. An example may be a primary city receives 0.25 inches of rain then based on previous historical data for surrounding geographic locations historical data a suburb where the user's property is located may receive at least 0.20 inches of rain, and with such date the AI reviews this data from other regions and may make informed decisions based on the specific irrigation site. This third mechanism may be utilized alone or in conjunction with the first feature and second feature to provide input for the AI to make an informed decision and adjustment to the irrigation system.

Additional inputs are contemplated and expected such as local watering laws and ordinances as well as local utility information for water usage. Each of these different inputs into the system allow the system to self-manage with the AI feature providing better watering and appropriate water conservation.

DETAILED DESCRIPTION

Figure 1:
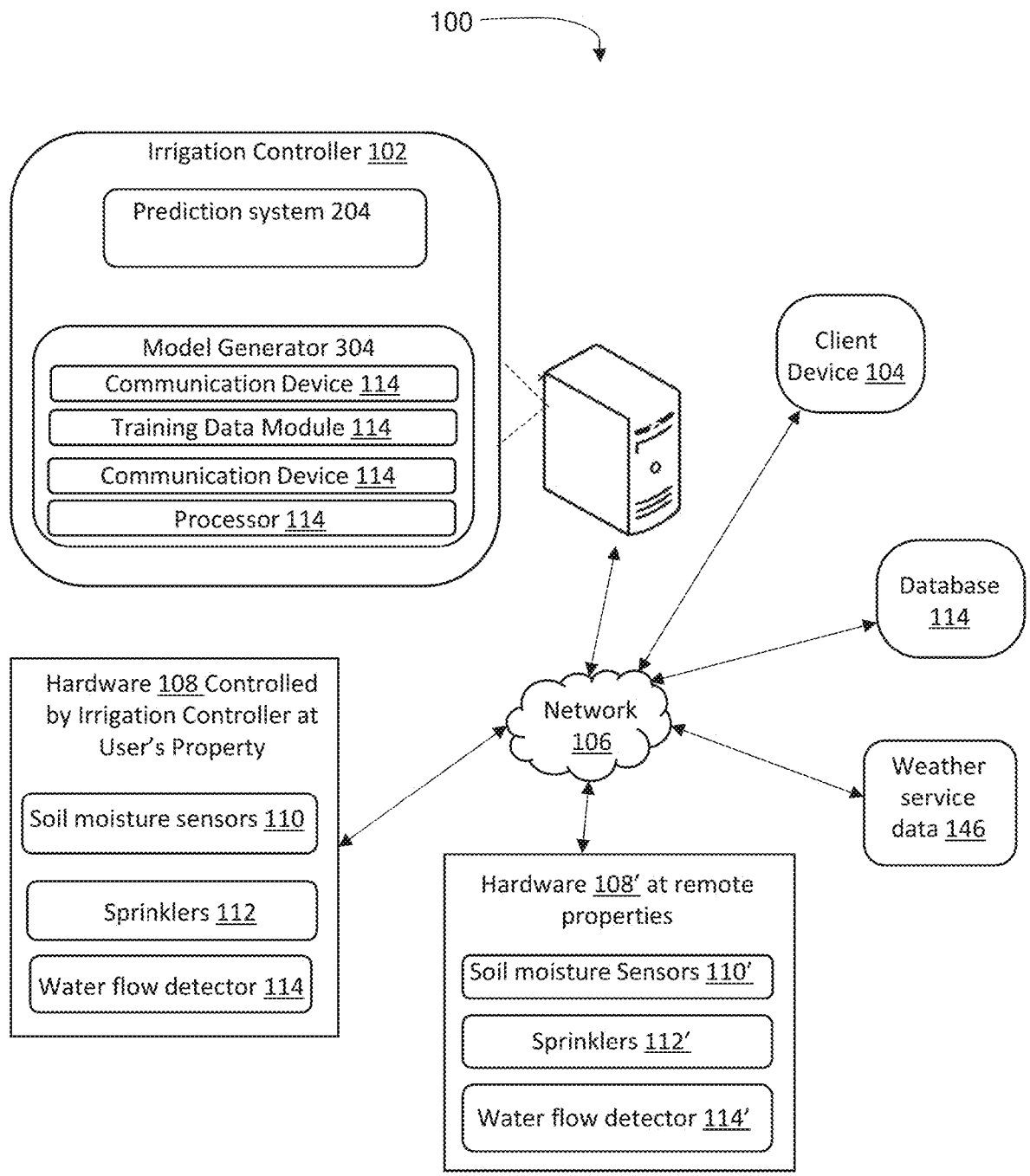
FIG. 1 is a block diagram of an irrigation system, in accordance with disclosed embodiments.

Before the present invention is disclosed and described in detail, it should be understood that the present disclosure is not limited to any particular structures, process steps, or materials discussed or disclosed herein, but is extended to include equivalents thereof as would be recognized by those of ordinary skill in the relevant art. More specifically, the invention is defined by the terms set forth in the claims. The discussion of any particular aspect of the invention is not to be understood as a requirement that such aspect must be present apart from an express inclusion of the aspect in the claims. As used in this specification and the appended claims, singular forms such as "a," "an," and "the" may include the plural unless the context clearly dictates otherwise. Thus, for example, reference to "a watering instruction" may include one or more of such watering instructions, and reference to "the moisture sensor" may include reference to one or more of such moisture sensors.

In the present document, the word "exemplary" is used herein to mean "serving as an example, instance, or illustration." Any embodiment or implementation of the present subject matter described herein as "exemplary" is not necessarily to be construed as preferred or advantageous over other embodiments. It will also be appreciated by those skilled in the art that the words during, while, and when as used herein are not exact terms that mean an action takes place instantly upon an initiating action but that there may be some small but reasonable delay, such as a propagation delay, between the initial action and the reaction that is initiated by the initial action. Additionally, the word "connected" and "coupled" is used throughout for clarity of the description and can include either a direct connection or an indirect connection.

The following description sets forth a system, for managing irrigation and watering either residentially, commercially or agriculturally. The system may include multiple inputs from a plurality of sources to appropriately provide enough information to the system so that the ideal amount of moisture to a landscape is administered.

The disclosure is also directed to a machine learning artificial intelligence system for predicting soil moisture levels at a property and communicating them to an irrigation system to execute watering instructions at the property based on the predictive soil moisture levels. The artificial intelligence system may model a property's soil moisture levels using various data, such as third party weather data at a remote location, system weather data at a remote location, soil moisture levels at a remote location, and water flow data at a remote location or from a local utility company. As used herein, "triggering event" comprises any event that the system determines could lead to a change in a property's soil moisture levels and includes, without limitation, weather service data for a location remote from the property, third party weather service data, and data taken from an extended network of irrigation systems, such as weather data at a remote property in the extended network, soil moisture levels at a remote property in the extended network, and/or water flow data at a remote property in the extended network. As used herein, "remote" means a property other than the specific user's property. A remote property may be adjacent to the user's property, and may also include, for example, properties within a specific radius, such as a 5-mile radius, 10-mile radius, 20-mile radius, etc. Remote properties may also be referred to herein as "a second property" and the user's property may be referred to as "a first property," "user's property," and/or "client's property."

In some embodiments, the system may continuously or nearly continuously request a prediction for soil moisture content at the property. The prediction system may analyze data from remote properties or locations, such as soil moisture data at a remote location, using prediction models. The prediction models may be generated using machine learning algorithms that study training data sets that associate the data received with corresponding "ground truth," that is, information provided by direct measurement of soil moisture levels by soil moisture sensors at the property as opposed to information provided by prediction. The machine learning algorithms may update and tailor the prediction models based on the ground truth. The prediction system may output a prediction of soil moisture levels at the property based on the analysis of data from remote locations, such as soil moisture data at a remote location. The prediction system may, for example, determine a soil moisture function that maps predictive soil moisture to the data received. The prediction system may then store the soil moisture function, along with metadata associated with the triggering event (such as a location of the triggering event, time of day, date, air temperature, length/volume/rate of triggering event, etc.). The stored soil moisture functions may be retrieved at a later time to make a future soil moisture level prediction.

In some embodiments, the prediction system may be coupled with databases that store historical weather data and use data processing methods to curate information and facilitate data analysis. In other embodiments, the prediction system may improve accuracy by using iterative methods in which multiple prediction models are generated and then aggregated. In yet other embodiments, the prediction system may include hardware configured to efficiently conduct filtering, sorting, and parallel calculation tasks to improve computing time and cost.

FIG. 1 shows illustrates an exemplary implementation 100 of an artificially intelligent irrigation system, implemented in a network 106, according to an embodiment of the present disclosure. Systems and methods are described herein for providing a method and system for using artificial intelligence to predict soil moisture levels, and in turn using the predictive moisture levels to control an irrigation system, including an irrigation controller 102 in communication with hardware 108 at the user's property, such as sprinklers 112. The system 100 may be used to predict soil moisture content at a specific property having an irrigation system, and then may be used to direct hardware, such as sprinklers 112, to either provide more or less water to the property based on the prediction. The system may include a prediction system 204, a model generator 304, and one or more of the following connected via a network 106: client devices 104, databases 114, weather service data 146, hardware 108 at the first property, and hardware 108' at one or more remote properties. In some embodiments, as shown in FIG. 1, each component of system 100 may be connected to a network 106. However, in other embodiments components of system 100 may be connected directly with each other, without network 106. Additional components may be part of the system, and the prediction system may take into consideration data from additional inputs, such as data from a local water utility, etc.

The network 106 may be a wireless or a wired network, or a combination thereof. The network 106 can be a collection of individual networks, interconnected with each other and functioning as a single large network (e.g., the internet or an intranet). Examples of such individual networks include, but are not limited to, Global System for Mobile Communication (GSM) network, Universal Mobile Telecommunications System (UMTS) network, Personal Communications Service (PCS) network, Time Division Multiple Access (TDMA) network, Code Division Multiple Access (CDMA) network, Next Generation Network (NGN), Public Switched Telephone Network (PSTN), and Integrated Services Digital Network (ISDN). Depending on the technology, the network 106 includes various network entities, such as gateways, routers; however, such details have been omitted for ease of understanding.

Weather service data 146 may be a system associated with a third party weather service, such as an entity that provides weather data. Weather service data 146 may store information about weather that includes, for example, precipitation data, and specific data associated with the precipitation data, such as the time of day of precipitation, the location and amount of precipitation, the date of precipitation, the temperature at the time of precipitation, and/or other weather data known to those skilled in the art.

Client devices 104 may include software that when executed by a processor performs known Internet-related communication and content display processes. For instance, client devices 104 may execute browser software that generates and displays interfaces including content on a display device included in, or connected to, client devices 104. Client devices 104 may execute applications that allows client devices 104 to communicate with components over network 106, and generate and display content in interfaces via display devices included in client devices 104. The disclosed embodiments are not limited to any particular configuration of client devices 104. For instance, a client device 104 may be a mobile device that stores and executes mobile applications that provide functions offered by prediction system 204 and/or hardware 108, such as moisture sensors.

Databases 114 may include one or more computing devices configured with appropriate software to perform operations consistent with providing prediction system 204 and model generator 304 with data associated with historical weather data and other triggering events. Databases 114 may include, for example, Oracle™ databases, Sybase™ databases, or other relational databases or non-relational databases, such as Hadoop™ sequence files, HBase™, or Cassandra™ Database(s) 180 may include computing components (e.g., database management system, database server, etc.) configured to receive and process requests for data stored in memory devices of the database(s) and to provide data from the database(s).

Data associated with weather may include, for example, historical weather data identifying precipitation and associated data there with, such as location of the precipitation, data identifying the measured amount of precipitation over time, data describing the date and time of the precipitation, data indicating the air temperature at time of precipitation, etc. While databases 114 are shown separately, in some embodiments databases 114 may be included in or otherwise related to one or more of prediction system 204 and model generator 304.

Databases 114 may be established on a local server, a remote server, on the cloud, etc., and may be configured to collect and/or maintain the data from the weather, the remote moisture flow sensors, and/or the remote soil moisture sensors and provide it to the prediction system 204, model generator 304, and client devices 104. Databases 114 may collect the data from a variety of sources, including, for instance, historical weather data, third party weather data, model generator 304, local water utilities, and/or third-party systems (not shown). Other sources of data associated with weather are possible as well.

Prediction system 204 may include one or more computing systems configured to perform one or more operations consistent with modeling the soil moisture levels of a specific property. Prediction system 204 may generate a prediction result based on the information received from one or more of, for example, weather service data 146, online resources, hardware 108, remote hardware 108', database 114, etc. Data relevant to the prediction system may include real-time water flow data, real-time precipitation data, real-time air temperature data, real-time soil temperature data, and/or real-time soil moisture level data. Prediction system 204 may determine a soil moisture function that maps predictive soil moisture to the data received. Prediction system 204 is further described below in connection with FIG. 2.

Model generator 304 may include one or more computing systems configured to generate prediction models to estimate soil moisture at a specific property using the weather and/or watering data in relation to ground truth soil moisture levels. Model generator 304 may receive or obtain information from databases 114, hardware 108', hardware 108, and/or weather data service 146.

In some embodiments, model generator 304 may receive a specific request from prediction system 204. In other configurations, model generator does not receive a specific request from prediction system, but rather begins generating prediction models automatically as soon as the model generator is turned "on" by a client. Prediction models may include statistical algorithms that are used to determine the probability of an outcome, given a set amount of input data. For example, prediction models may include regression models that estimate the relationships among input and output variables. Prediction models may also sort elements of a dataset using one or more classifiers to determine the probability of a specific outcome. Prediction models may be parametric, non-parametric, and/or semi-parametric models.

In some embodiments, prediction models may cluster points of data in functional groups such as "random forests." Random Forests may comprise combinations of decision tree predictors. (Decision trees may comprise a data structure mapping observations about something, in the "branch" of the tree, to conclusions about that thing's target value, in the "leaves" of the tree.) Each tree may depend on the values of a random vector sampled independently and with the same distribution for all trees in the forest. Prediction models may also include artificial neural networks. Artificial neural networks may model input/output relationships of variables and parameters by generating a number of interconnected nodes which contain an activation function. The activation function of a node may define a resulting output of that node given an argument or a set of arguments. Artificial neural networks may generate patterns to the network via an "input layer" which communicates to one or more "hidden layers" where the system determines regressions via a weighted connections. Prediction models may additionally or alternatively include classification and regression trees, or other types of models known to those skilled in the art. Each of these prediction models may be used alone or in combination with others. Model generator 304 may submit models to predict soil moisture levels. To generate prediction models, model generator 304 may analyze information applying machine-learning methods. Model generator 304 may communicate back with prediction system 204 via network 106 or other communication avenues. Model generator 304 is further described below in connection with FIG. 3.

FIG. 1 shows prediction system 204 and model generator 304 as a different components. However, prediction system 204 and model generator 304 may be implemented in the same computing system. For example, prediction system 204 and model generator 304 may be embodied in a single server. Network 106 may be any type of network configured to provide communications between components of system 100. For example, network 106 may be any type of network (including infrastructure) that provides communications, exchanges information, and/or facilitates the exchange of information, such as the Internet, a Local Area Network, near field communication (NFC), optical code scanner, or other suitable connection(s) that enables the sending and receiving of information between the components of system 100. In other embodiments, one or more components of system 100 may communicate directly through a dedicated communication link(s).

It is to be understood that the configuration and boundaries of the functional building blocks of system 100 have been defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Figure 2:
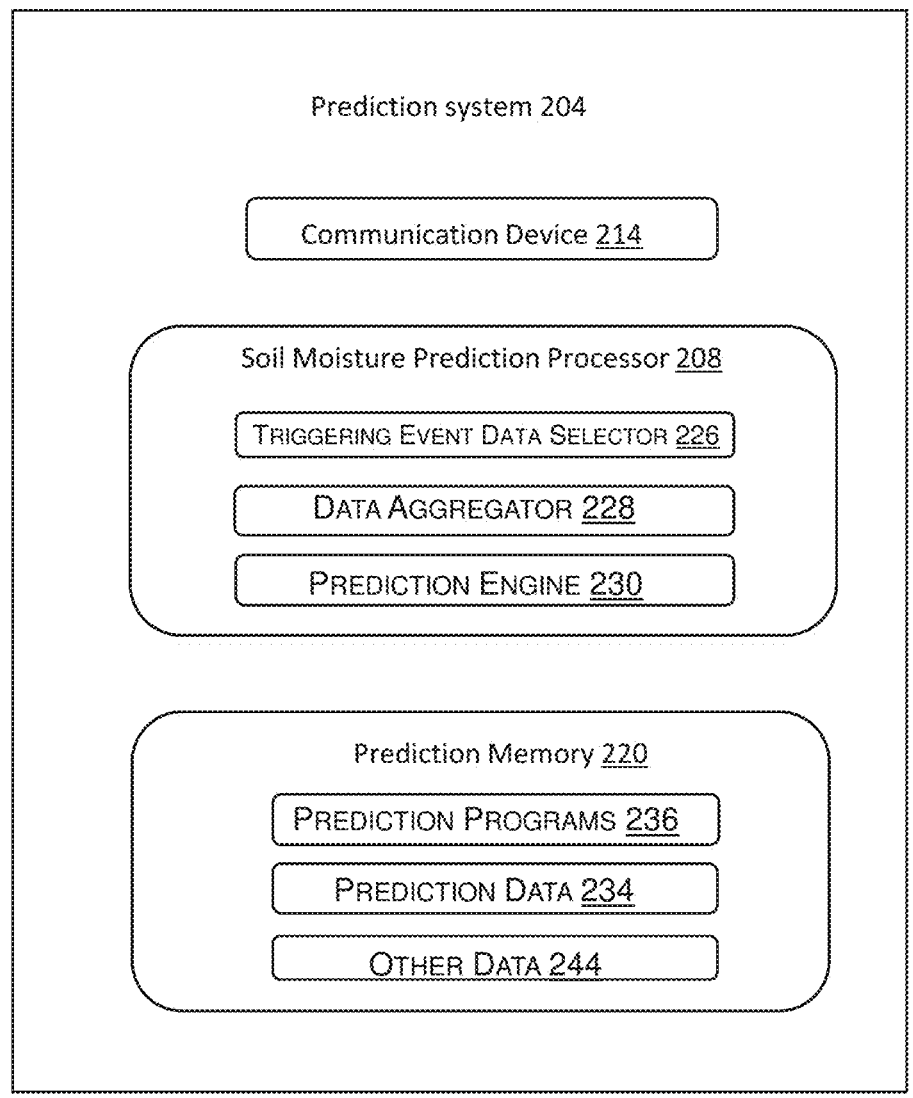
FIG. 2 is a block diagram of an exemplary prediction system, in accordance with disclosed embodiments.

FIG. 2 shows a block diagram of an exemplary prediction system 204, in accordance with disclosed embodiments. Prediction system 204 may include a communication device 214, a prediction memory 220, and one or more prediction processors 208. Prediction memory 220 may include prediction programs 236, prediction data 234, and other data 244. Prediction processor 208 may include triggering event data selector 226, data aggregator 228, and prediction engine 230.

In some embodiments, prediction system 204 may take the form of a server, general purpose computer, mainframe computer, or any combination of these components. Other implementations consistent with disclosed embodiments are possible as well. Communication device 214 may be configured to communicate with one or more databases 114, weather service data 146, hardware 108' hardware 108, etc. In particular, communication device 214 may be configured to receive inputs from hardware at remote properties data associated with triggering events. In addition, communication device 214 may be configured to communicate with other components as well, including, for example, a model generator 304. Communication device 214 may include, for example, one or more digital and/or analog devices that allow communication device 214 to communicate with and/or detect other components, such as a network controller and/or wireless adaptor for communicating over the Internet. Other implementations consistent with disclosed embodiments are also possible.

Prediction memory 220 may include one or more storage devices configured to store instructions used by soil moisture prediction processor 208 to perform functions related to disclosed embodiments. For example, prediction memory 220 may store software instructions, such as prediction program 236, which may perform one or more operations when executed by prediction processor 208. The disclosed embodiments are not limited to separate programs or computers configured to perform dedicated tasks. For example, prediction memory 220 may include a single prediction program 236 that performs the functions of prediction system 204, or prediction program 236 may comprise multiple programs. Prediction memory 220 may also store prediction data 234 that is used by prediction program(s) 236.

In certain configurations, prediction memory 220 may store sets of instructions for carrying out processes to model soil moisture levels at a specific property, generate a soil moisture prediction schedule, and/or generate a soil moisture function that maps predictive soil moisture to the data from the triggering event, described in connection with FIGS. 6-9. In general, instructions may be executed by prediction processor 208 to perform one or more processes consistent with disclosed embodiments. In some embodiments, soil moisture prediction processor 208 may include one or more known processing devices, such as, but not limited to, microprocessors from the Pentium™ or Xeon™ family manufactured by Intel™, the Turion™ family manufactured by AMD™, or any of various processors from other manufacturers. However, in other embodiments, soil moisture prediction processor 208 may be a plurality of devices coupled and configured to perform functions in accordance with the disclosure. The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), flash memory, and/or non-volatile storage. Other hardware, conventional and/or custom, may also be included.

Soil moisture prediction processor 208 may include a data selector 226, a data aggregator 228, and a prediction engine 230. In some embodiments, soil moisture prediction processor 208 may execute software to perform functions associated with each component of soil moisture prediction processor 208. In other embodiments, each component of prediction processor 208 may be an independent device. In such embodiments, each component may be hardware configured to specifically process data or perform operations associated with modeling soil moisture levels, generating prediction models and/or handling large data sets. For example, data selector 226 may be a field-programmable gate array (FPGA), data aggregator 228 may be a Graphics processing unit (GPU), and prediction engine 230 may be a central processing unit (CPU). Other hardware combinations are also possible. In yet other embodiments, combinations of hardware and software may be used to implement soil moisture prediction processor 208.

Data selector 226 may select data from hardware 108', weather service data 146, and/or database 114 based on parameters that indicate the data may have an effect on a specific property. That is, data selector may determine which, of all the data, is indicative of a triggering event. The system itself may learn over time which data is indicative of triggering events. For example, if the system determines that there is a precipitation event at a second property (either by hardware 108' located at the second property, weather service data 146, etc.), it may delay a watering event at the user's property and monitor the soil moisture levels at the user's property. Over time, the system may learn the causation associated between the soil moisture levels at the user's property and the triggering events.

Data selector 226 may select a subset of data that are associated with a triggering event by filtering the data set. The data set may be filtered based on location, for example. Data from locations within a certain radius of the user's property may be used. The radius may be very large depending on the location of user's property, and data from remote locations may also be taken based on weather patterns without regard for the distance from the remote location to the user's property. The data may be further filtered by a predetermined threshold amount. For example, a very small change in soil moisture at a remote property may be immediately filtered out as a non-triggering event. In some embodiments, data selector 226 may employ techniques, as not limiting examples, such as the pigeonhole principle, hierarchical verification, and the PEX algorithm, to filter and select data received.

In some embodiments, soil moisture prediction processor 208 may implement data selector 226 by executing instructions to create an environment in which historical weather data are selected. In other embodiments, however, data selector 226 may be a separate device or group of devices. In such embodiments, data selector 226 may include hardware configured to carry out filtering tasks. For example, to improve performance and minimize costs, data selector 226 may be an SRAM-based FPGA that functions as a data selector. Data selector 226 may have an architecture designed for implementation of specific algorithms. For example, data selector 226 may include a Simple Risc Computer (SRC) architecture or other reconfigurable computing system.

Data aggregator 228 may create a soil moisture function to maps predictive soil moisture to the data received. The soil moisture function may represent an aggregate function of ground truth soil moisture level at the property for historical triggering events determined most similar to the current triggering event.

Soil moisture prediction processor 208 may implement data aggregator 228 by executing software to create an environment for aggregation of soil moisture functions representative of historical triggering events. However, in other embodiments data aggregator 228 may include independent hardware with specific architectures to improve the efficiency of aggregation or sorting processes. For example, data aggregator 228 may be a GPU array configured to sort historical triggering events and their associated functions and metadata. In some embodiments, data aggregator 228 may be configured to implement sorting algorithms such as, for example, radix sort. Alternatively or additionally, data aggregator 228 may be configured to implement a programming interface, such as Apache Spark, and execute data structures, cluster managers, and/or distributed storage systems. For example, data aggregator 228 may include a resilient distributed dataset that is manipulated with a stand-alone software framework and/or a distributed file system.

Prediction engine 230 may calculate a prediction indication based on one or more models and a selected data set. For example, prediction engine 230 may use a model from model generator 304 and apply inputs based on a triggering event to generate a prediction value for soil moisture levels for a specific property. Prediction engine may use a model from model generator 304 and determine a soil moisture function that maps predictive soil moisture to the triggering event data.

Prediction engine 230 may be implemented by soil moisture prediction processor 208. For example, prediction processor 208 may execute software to create an environment to execute models. However, in other embodiments prediction engine 230 may include hardware configured to carry out parallel operations. Some hardware configurations improve the efficiency of calculations, particularly when multiple calculations are being processed in parallel. For example, prediction engine 230 may include multicore processors or computer clusters to divide tasks and quickly perform calculations. In some embodiments, prediction engine may receive a plurality of models from model generator 304. In such embodiments, prediction engine 230 may include a scheduling module. The scheduling module may receive models and assign each model to independent processors or cores. In other embodiments, prediction engine 230 may be FPGA Arrays to provide greater performance and determinism.

The components of prediction system 204 may be implemented in hardware, software, or a combination of both, as will be apparent to those skilled in the art. For example, although one or more components of prediction system 204 may be implemented as computer processing instructions embodied in computer software, all or a portion of the functionality of prediction system 204 may be implemented in dedicated hardware. For instance, groups of GPUs and/or FPGAs may be used to quickly analyze data in prediction processor 208.

Figure 3:
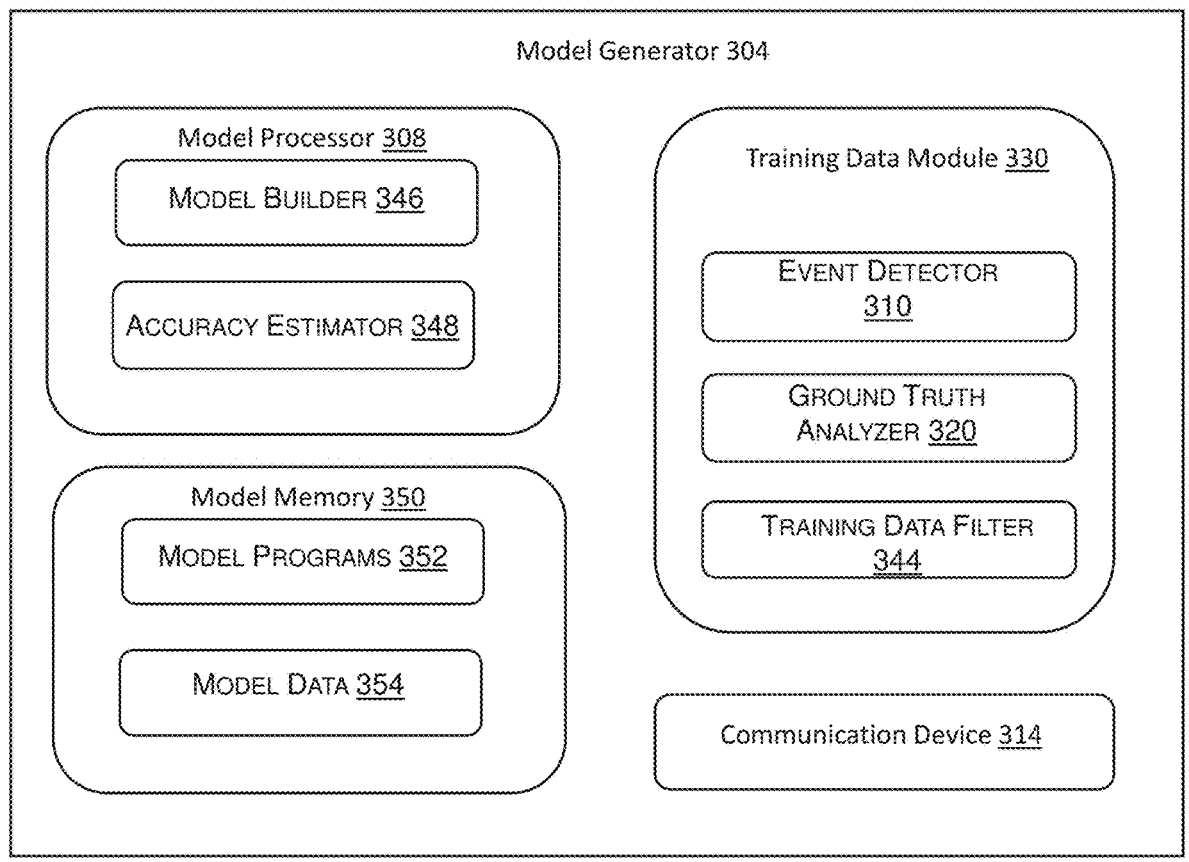
FIG. 3 is a block diagram of an exemplary model generator, in accordance with disclosed embodiments.

FIG. 3 is a block diagram of an exemplary model generator, in accordance with disclosed embodiments. Model generator 304 may include training data module 330, a model processor 308, a model memory 350, and a communication device 314.

One of the fundamental challenges in obtaining accurate soil moisture predictions based on triggering events such as precipitation received at a remote location, or a watering event at a remote location, is the lack of sufficient training data sets. Training sets are sets of data used to discover potentially predictive relationships. They may include an input vector and an answer vector, that are used together to train an AI machine or a knowledge database. A training data set may only be sufficient when it includes a number of samples that enables an artificial intelligence machine or a regression model to be "trained" (e.g., initialized) with an acceptable confidence interval. Sufficient training data sets may include samples that represent the full distribution to be modeled and have enough samples to identify outliers and minimize deviations. In some embodiments, training data sets include a validation subset and a test subset. In such embodiments, each one of the subsets must include a representative sample size.

Figure 4:
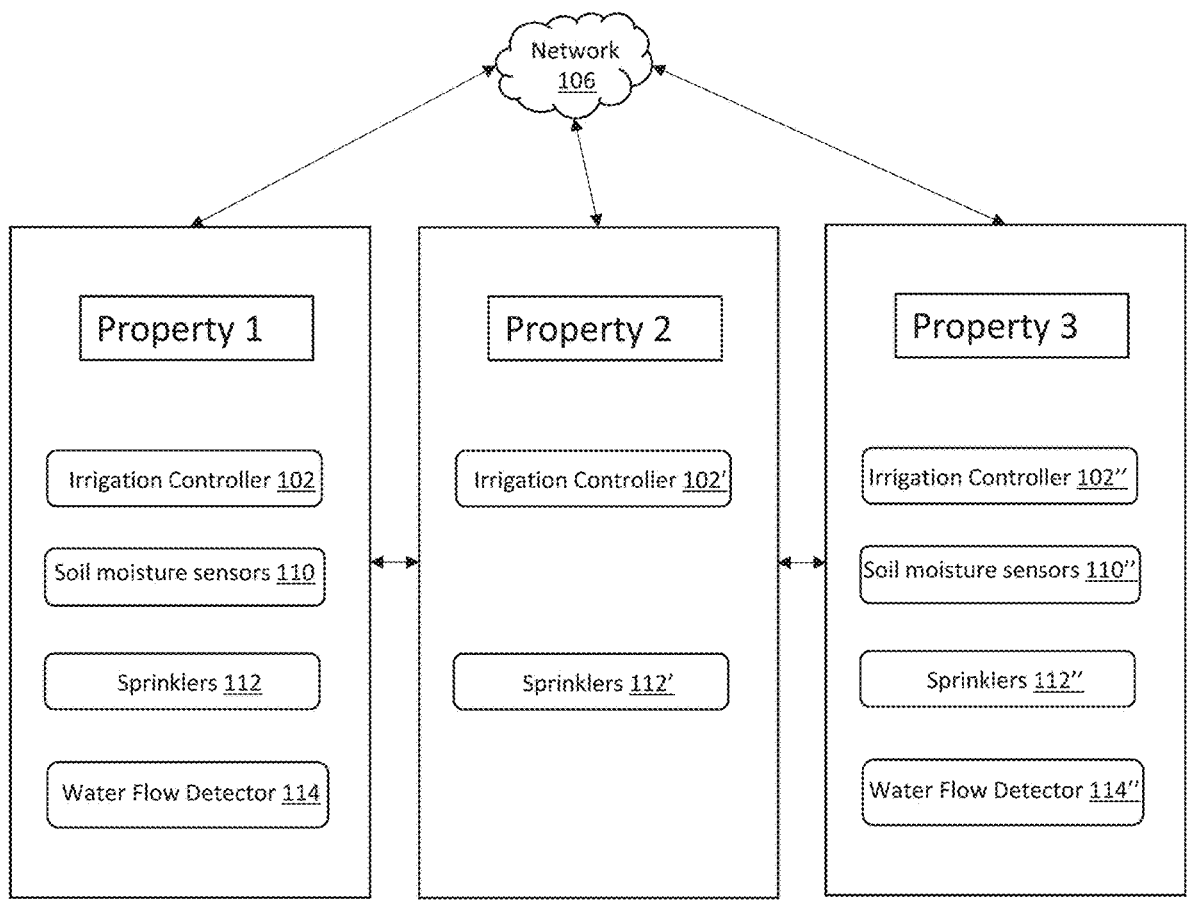
FIG. 4 is a block diagram of an exemplary extended irrigation network.
Figure 5:
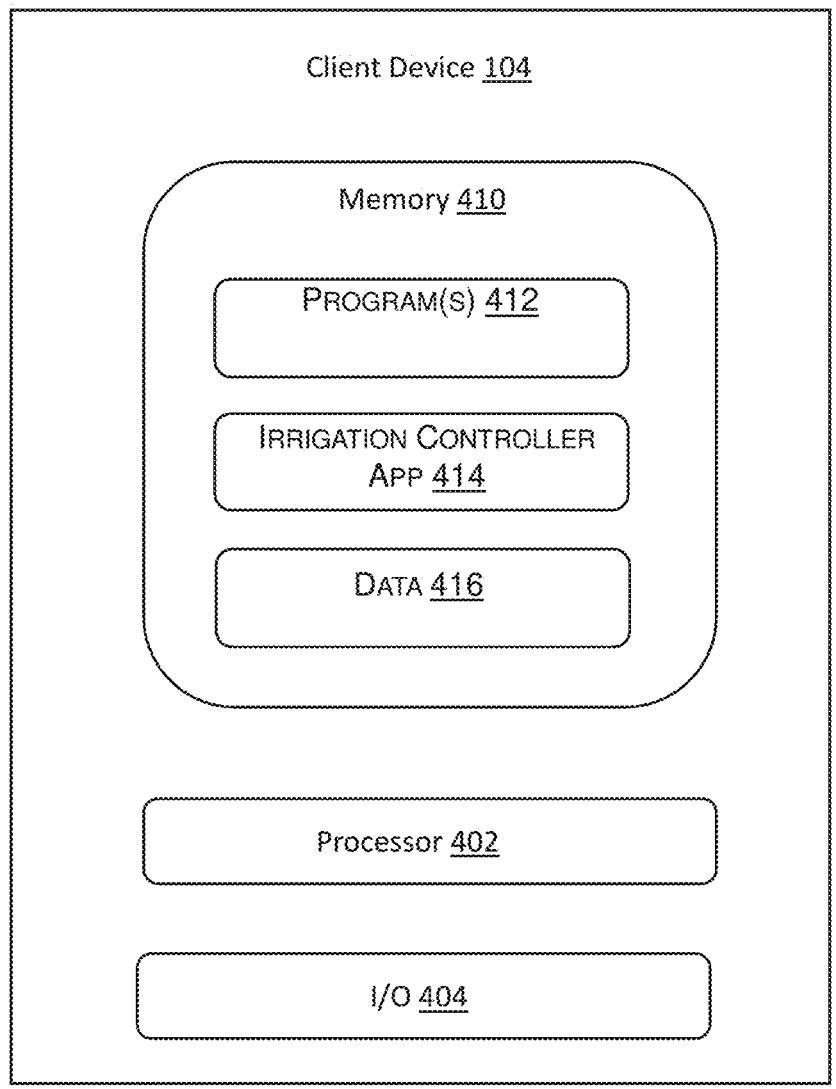
FIG. 5 is a block diagram of an exemplary client device.

In some embodiments, training data sets associate triggering events, such as a measured precipitation at a remote location, with ground truth soil moisture levels within a predetermined amount of time of the triggering event, that is, actual soil moisture levels measured at a specific property and obtained directly or indirectly from the moisture level sensor at the property within the predetermined amount of time. In other configurations, training data sets associate soil moisture data and/or water flow data from a second property with ground truth soil moisture levels, that is, actual soil moisture levels measured at the specific first property and obtained directly or indirectly from the moisture level sensor at the first property within a predetermined amount of time. FIG. 4 shows a representative extended network of irrigation controllers at three different properties. The irrigation controllers may be connected to each other via a network 106, or alternatively, individual components of the irrigation system may be connected via a network, such as LoRa, Zigbee, etc. For example, soil moisture sensors 110 at Property 1 may be able to communicate data relating to their measurements directly to a soil moisture sensor at Property 3 in a relay-type network that may allow extended communication even in the absence of wireless or other available networks.

Training data sets may include information from multiple properties that are connected together in a larger irrigation system. The system may act as a central source for ground truth of the soil moisture levels for each specific property. Even more, the system may act as a central source for ground truth of the soil moisture levels for each specific moisture sensor on each property, as multiple moisture sensors on each property each may have a unique moisture level, particularly where the property is large and has varying landscape features. In some embodiments model generator 304 may include a training data module 330 that monitors network 106 to capture ground truth and facilitate generating the training data set. Training data module 330 may combine and select information to generate the training data sets used to generate prediction models.

Training data module 330 includes an event detector 310 and ground truth analyzer 320, and training data filter 344. Event detector 310 may be a software or hardware module configured to detect events in network 106 that may be relevant to model generator 304. In some embodiments, event detector 310 may be configured to detect when a specific property waters (such as by detecting water flow at the specific property with a water flow meter). In such embodiments, event detector 310 may signal model generator 304 to request the water flow measurement at the second property, as well as the ground truth soil moisture level at the first property after a predetermined amount of time, and build the training data set.

In addition, event detector 310 may be configured to detect changes in soil moisture at a specific property. For example, if a remote property within a 5 mile radius of the client's property has the soil moisture increase without a measurement of water flow, event detector 310 may request the soil moisture increase at the remote property, the associated ground truth soil moisture level at the first property after a predetermined amount of time, and determine a soil moisture function that maps the ground truth soil moisture level to the triggering event at the remote property, and build the training data set. Event detector 310 may create a system to automatically update a training data set of soil moisture levels. The ground truth soil moisture may also be compared to weather data to determine if change in soil moisture levels can be attributed to a watering event, weather precipitation, etc. The data training set may also be programmed to include, or in some configurations may automatically include, a predetermined acceptable threshold level for triggering events. For example, a very small increase in soil moisture at a remote property may be below the predetermined acceptable threshold level and thus may not qualify as a triggering event for the user's property. The predetermined acceptable threshold level may be different for different properties based on soil types.

Ground truth analyzer 320 may include software or hardware modules configured to collect and organize data that is associated with a specific property. Ground truth analyzer 320 may also collect and organize data associated with other properties within a larger network.

Training data module 330 may include software or hardware modules configured to create a training data set. Training data module 330 may create the training data set by combining data for triggering events from a group of a specific properties and ground truth information for the same group of a specific properties. For example, communication device 314 may receive a collection of data associated with a triggering event generated by a group of a specific properties. If ground truth analyzer 320 has identified soil moisture levels after a predetermined amount of time after the triggering event about the same group of a specific properties, training data module 330 may combine these data sets to create a training data set that includes triggering event data and ground truth for a group of a specific properties. This may be extended over a broad network.

Training data filter 344 may have a similar configuration to triggering event data selector 226 but instead of filtering data associated that may indicate a triggering event for a specific property, training data filter 344 may select a training data subset before it is used to generate models. The accuracy of the model used to predict soil moisture levels may vary significantly when different data sets are used. For example, predicting soil moisture levels of the client's property in January using a training data set that is based on models for July may undermine the prediction's accuracy. For this reason, training data filter 344 may be configured to select training data sets based on, for example, the type of triggering event. Then, the training data set may be constrained to certain types of historical triggering events or models.

Model processor 308 may include a processor similar to prediction processor 208. Model processor may include a model builder and optionally an accuracy estimator.

Model builder 346 may be software or hardware configured to create prediction models based on the training data. Such prediction models may include functions that map the measured ground truth soil moisture levels to the triggering event data. In some embodiments, model builder 346 may generate decision trees. For example, model builder 346 may take training data to generate nodes, splits, and branches in a decision tree. Model builder 346 may calculate coefficients and hyper parameters of a decision tree based on the training data set. In other embodiments, model builder 346 may use Bayesian algorithms or clustering algorithms to generate predicting models. In yet other embodiments, model builder 346 may use association rule mining, artificial neural networks, and/or deep learning algorithms to develop models. In some embodiments, to improve the efficiency of the model generation, model builder 346 may be hardware configured to generate models for soil moisture levels. For example, model builder 346 may be an FPGA.

Accuracy estimator 348 may be software or hardware configured to evaluate the accuracy of a model. For example, accuracy estimator may estimate the accuracy of a model, generated by model builder 346, by using a validation dataset. In some embodiments, the validation data set is a portion of the training data set that was not used to generate the prediction model. Accuracy estimator may generate error rates for each one of the prediction models. Accuracy estimator 348 may additionally assign weight coefficients to models based on the estimated accuracy. In some configurations, an accuracy estimator is not used, as the system may track ground truth soil moisture and use it determine accuracy of the model in real-time. Additionally, if the model is not accurate, the system may take corrective steps as a result For example, if the system had delayed a watering event due to a predicted increase in soil moisture levels, and the soil moisture level did not increase, the system could proceed with the delayed watering event. Model memory 350 may include model programs 352 and model data 354.

FIG. 4 is a block diagram of one embodiments of a client device 104, in accordance with disclosed embodiments. In one embodiment, client devices 104 may include one or more processors 402, one or more input/output (I/O) devices 404, and one or more memories 410. In some embodiments, client devices 105 may take the form of mobile computing devices such as smartphones or tablets, general purpose computers, or any combination of these components. Alternatively, client devices 104 (or systems including client devices 104) may be configured as a particular apparatus, embedded system, dedicated circuit, and the like based on the storage, execution, and/or implementation of the software instructions that perform one or more operations consistent with the disclosed embodiments. According to some embodiments, client devices 104 may comprise web browsers or similar computing devices that access a web site, for example with web-based software, consistent with disclosed embodiments. In one implementation the system 100 is connected to one or more client devices 104-1, 104-2, 104-3, etc., individually and commonly referred to as client device(s) 104 hereinafter, through a communication network 106. The client devices 104 may provide specific watering instructions, and may also be used to inform and/or alert the client about watering steps taken by the irrigation system and the state of the irrigation system. The client devices 104 may serve both to provide specific instructions regarding watering, and to provide the client with the real-time status of the system and the watering actions the system intends to make based on the prediction system. Such client devices 104 include, but are not limited to, desktop computers, hand-held devices, laptops or other portable computers, tablet computers, mobile phones, PDAs, Smartphones, Smart energy meters, Smart home monitoring systems, smart electric appliances, and the like. Further, the client devices 104 may include devices capable of exchanging data to provide connectivity to different communicating devices and computing systems. Such devices may include, but are not limited to, data cards, mobile adapters, wireless (WiFi™) adapters, routers, a wireless modem, a wireless communication device, a cordless phone, a wireless local loop (WLL) station, and the like. As client devices 104 may be stationary or mobile and may also be understood to be a mobile station, a terminal, an access terminal, a subscriber unit, a station, etc.

Processor 402 may include one or more known processing devices, such as mobile device microprocessors manufactured by Intel™, NVIDIA™, or various processors from other manufacturers. The disclosed embodiments are not limited to any specific type of processor configured in client devices 104. Memory 410 may include one or more storage devices configured to store instructions used by processor 402 to perform functions related to disclosed embodiments. For example, memory 410 may be configured with one or more software instructions, such as programs 412 that may perform one or more operations when executed by processor 402. The disclosed embodiments are not limited to separate programs or computers configured to perform dedicated tasks. For example, memory 410 may include a single program 412 that performs the functions of the client devices 104, or program 412 may comprise multiple programs. Memory 410 may also store data 416 that is used by one or more programs 412, and/or an irrigation controller application 414.

I/O devices 404 may include one or more devices configured to allow data to be received and/or transmitted by client devices 104 and to allow client devices 104 to communicate with other machines and devices, such as other components of system 100. For example, I/O devices 404 may include a screen for displaying optical payment methods such as Quick Response Codes (QR), or providing information to the user. I/O devices 404 may also include components for NFC communication. I/O devices 404 may also include one or more digital and/or analog devices that allow a user to interact with client devices 104 such as a touch-sensitive area, buttons, or microphones. I/O devices 404 may also include one or more accelerometers to detect the orientation and inertia of client devices 104. I/O devices 404 may also include other components known in the art for interacting with prediction system 204. The components of client devices 104 may be implemented in hardware, software, or a combination of both hardware and software, as will be apparent to those skilled in the art.

Figure 6:
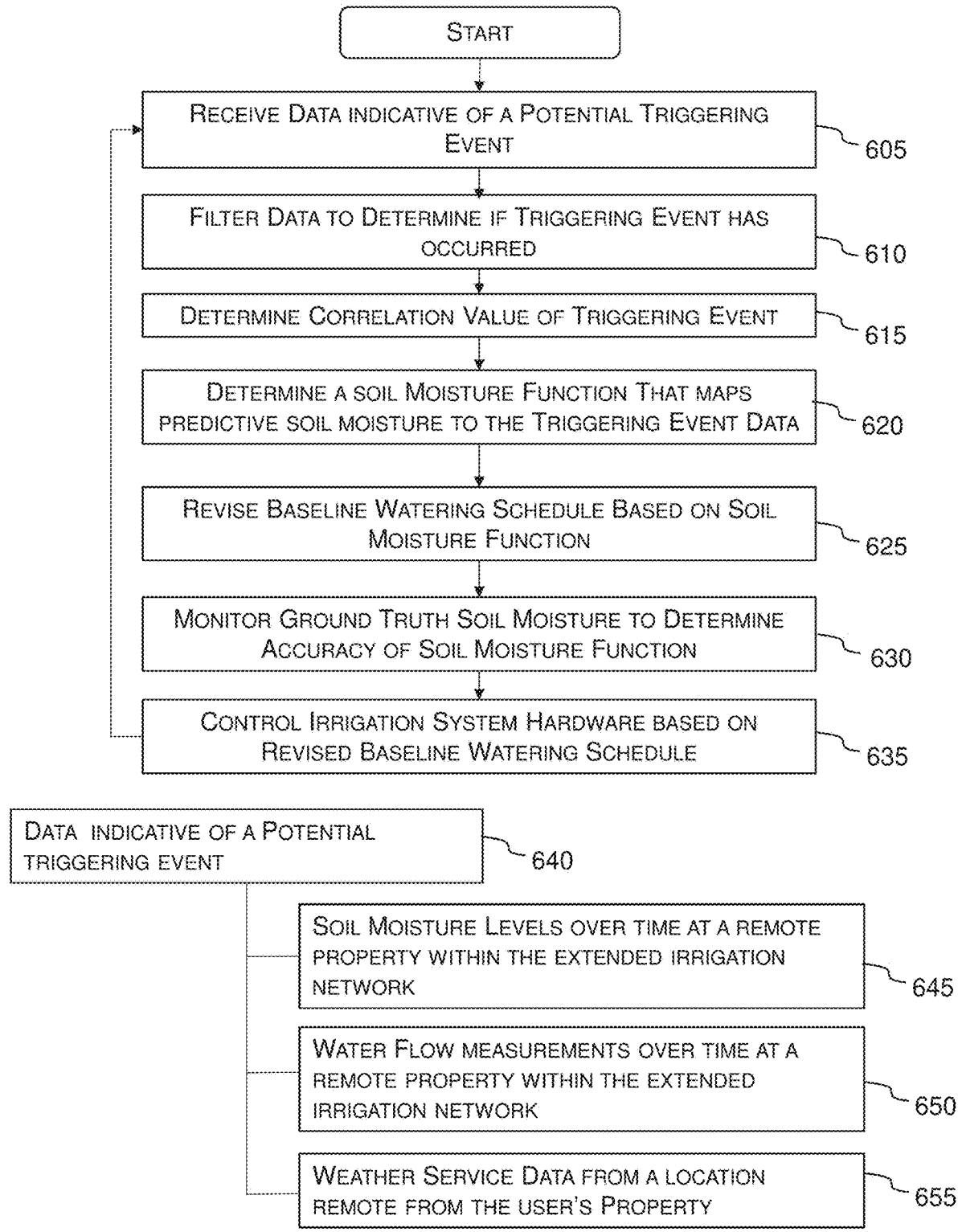
FIG. 6 is an exemplary flow chart illustrating a prediction process, in accordance with disclosed embodiments.

FIG. 6 is an exemplary flow chart illustrating a prediction process and steps taken to adjust an irrigation system watering schedule as a result of the prediction process according to disclosed embodiments. In some embodiments, prediction process may be executed by prediction system 204.

Prediction system 204 may constantly or nearly constantly receive data indicative of a potential triggering event, including data from weather services, hardware at remote properties, etc., in step 605. Data indicative of a potential triggering event (640 in FIG. 6) may include a measured change in soil moisture levels at a remote property (645), a measured watering event occurring at a remote property (650), a measured precipitation at a remote location (655), etc., and may further include data relating to the time of the triggering event, an air temperature, date of triggering event, etc. For example, triggering event may comprise data relating to the amount of precipitation, the location of the measured precipitation, the time of the event, and the air temperature at the time of the event. Additionally many more triggering events are contemplated including, but not limited to, utility water usage, evapotranspiration rates and others.

In step 610, prediction system 204 may filter, or select, a portion of the data received from the database based on information contained in the data received. For example, in embodiments where prediction system 204 retrieves all weather data for a geographic area, the prediction system may filter the weather data received to only data that is relevant to occurrences within a predetermined radius of the client's property, such as weather data for a 2-, 5-, 10-, 15-, 20-, 50-, 100-, 500-mile, or an even larger radius of the client's property. It also need not be an exact radius. For example, for some properties, the system may determine that weather data taken from properties west of the user's property may be more relevant in determining triggering events.

In some embodiments, prediction system 204 may filter weather service data to simplify future analysis. For example, prediction system may require that a precipitation event be measured above a specific threshold, such as above 0.1 inches. For precipitation events that are lower than the threshold, the prediction system may automatically filter them out. Similarly prediction system 204 may filter water flow data and/or moisture sensor data retrieved from other properties based on a change in percentage over time and/or a volume of flow. In such embodiments, data selector 226 may curate and classify weather service data, water flow data, and/or moisture sensor data. For example, data selector 226 may discard water flow data for locations that are considered too remote from the property, and/or may discard water flow data for locations that are below or "downstream" from the property, even if they are close in proximity. Similarly data selector 226 may disregarding water flow levels and/or precipitation data that are below a specific level as these may represent activity that is not related to soil moisture levels at the property. The data points that do not correlate with soil moisture levels at the property may be filtered based on distance from the property, not reaching a threshold level, or other parameters.

In some embodiments prediction system 204 and data selector 226 may use data-mining algorithms to efficiently curate, parse, and/or filter the weather service data, water flow measurements, and soil moisture levels. For example, prediction system 204 may use algorithms such as C4.5, Support Vector Machines, Apriori algorithm, Expectation-maximization algorithm, among others, to handle large data sets of historical weather data, real-time weather service data, water flow measurements, and soil moisture levels.

In step 615, prediction system 204 may determine whether the correlation of a triggering event (such as a change in water flow at a second property, a change in soil moisture levels at a second property, and/or a measurement of precipitation at a remote location from the property) and a ground truth soil moisture level at the property is sufficient to make an accurate prediction. In some embodiments, prediction system 204 may determine a threshold correlation over a period of time. For example, prediction system 204 may set a threshold correlation value. If the threshold is not met, then prediction system 204 may determine that the correlation value is not met, and the watering schedule at the property may not be changed based on the event. In yet other embodiments, prediction system 204 may determine the correlation is not sufficient if a requested prediction accuracy cannot be met. For example, the system may require a minimum prediction accuracy of 50%. If the available data cannot allow a correlation greater than the required predicted accuracy, the watering schedule at the property may not be changed as a result of the event. In other configurations, the required accuracy may be higher. However, the system need not require a perfectly accurate prediction to proceed, because the system may be able to constantly or nearly constantly check the accuracy of the prediction based on ground truth soil moisture sensors. Where the system determines the model was not accurate, the system may take corrective action, such as by performing a baseline watering event that was previously delayed based on the model. This "wait-and-see" approach to the predictive model may serve to save water, as the system may delay scheduled watering events by a short period of time even if there is only a 10% chance a soil moisture level may increase.

Correlation of the triggering event may be determined by comparing the present triggering event (including data associated with the present triggering event, such as the date, time of day, location, and volume/amount of triggering event) to historical stored triggering events with their associated data. In other configurations, there is no need for a minimum accuracy for the prediction value as the system can monitor the accuracy of the prediction in real-time based on ground truth soil moisture levels and adjust as needed.

In step 620, prediction system 204 may generate a function that maps the triggering event over time in relation to the ground truth soil moisture level at the property over time. For example, as the measured precipitation at a remote location increases over time, a delayed response may be seen in the soil moisture level at the property over time. The delay in the response may be a direct function of the distance from the remote location to the property, and also may be a function of the type of triggering event. Predicting a soil moisture increase at the client's property in response to a precipitation event at a remote location may allow the irrigation system at the client's property to effectively anticipate precipitation that will occur in the near future, and cancel a scheduled watering system in advance of the anticipated precipitation.

Similarly, prediction system 204 may generate a function that maps a triggering event such as a measured change in water flow at a second property, over time in relation to the real-time ground truth soil moisture at the property. For example, watering at the second property (as measured by the change in water flow) may predictably yield an increase in soil moisture levels at the client's property. This may be particularly true for adjacent properties and/or a client's property that is downstream or otherwise below the second property.

Step 620 may be carried out by prediction engine 230. Prediction engine may compute a probability of a specific property having a moisture level increase based on a triggering event. For example, in step 620 prediction system 204 may request from model generator 304 one or more models to predict soil moisture levels for a selected a specific property. Prediction system 204 may then send prediction models and data to prediction engine 230 to perform the probability calculations.

In some embodiments, prediction engine 230 may receive a plurality of functions from model generator 304 and compute probabilities independently for each one of the functions. Prediction engine 230 may then tally each one of the prediction model results. In such embodiments, prediction engine 230 may determine an accuracy value for each model and each model result. For example, based on the evaluation performed by accuracy estimator 348, prediction engine 230 may determine an accuracy value for each model and each model result. Then prediction engine 230 may assign weighting coefficients to the models based on the accuracy values. In such embodiments, prediction engine 230 may modify the computed probability for each one of the models (i.e. the model results) using the assigned weighting.

In step 625, prediction system 204 may communicate the results list to the irrigation controller, and the irrigation controller may take action automatically based on the predicted soil moisture level, by revising a scheduled baseline watering event. For example, if the irrigation controller was going to begin watering a property within the next 30 minutes, but the prediction system 204 predicts the soil moisture level will increase on the property in the next 60 minutes based on the triggering event at the remote location, the irrigation controller may automatically alter, delay or cancel the scheduled watering.

In step 630, the system may monitor ground truth soil moisture levels to determine the accuracy of the predictive soil moisture function. In this manner, the system may be constantly building the training data set, including for real-time events that the system made a prediction for. Additionally, by monitoring the ground truth soil moisture level, the system may make further adjustments, if needed. For example, if the soil moisture level at the client's property did not increase as predicted by the predictive soil moisture function, the AI may instruct the irrigation system to perform the previously delayed baseline watering event or alternatively adjust the scheduled watering to a shorter duration. In step 635, the irrigation controller may control the system hardware, such as sprinklers 112, based on the revised baseline schedule.

Generating a prediction soil moisture function may be carried out by prediction system 204. The prediction system 204 may obtain a model for the specific triggering event based on a correlation to a stored historical triggering event. In some embodiments, prediction system 204 may send a request to model generator 304 to generate prediction models for the specific triggering event. Model generator 304 may respond with one or more prediction models for the specific triggering event based on, for example, the classification of the type of triggering event and the location of the triggering event. For instance, model generator 304 may send to prediction system 204 a group of prediction models specifically for a watering event detected at an adjacent property to the client's property. Or model generator 304 may send to the prediction system 204 a group of prediction models specifically for a precipitation event detected at a nearby city.

Prediction system 204 may compare the correlation values of each prediction model, using the metadata associated with the stored historical triggering event along with the data relating to the present triggering event. Weights may be given to different aspects of the metadata. For example, the location of the triggering event may be given more weight than a date of the triggering event. The system may determine what features may be given specific weights, and system may change the weights based on the stored model features. For example, there may be a very strong correlation between the location of a precipitation event and moisture levels at the client's property, no matter what date or time of the precipitation. Similarly, there may be a strong correlation between a watering event at an adjacent property and moisture levels at the client's property, but only below a certain air temperature. Based on weighted correlation values of the prediction models, the system may select a specific prediction model, or the system may generate a new prediction model as a weighted average of the prediction models.

Figure 7:
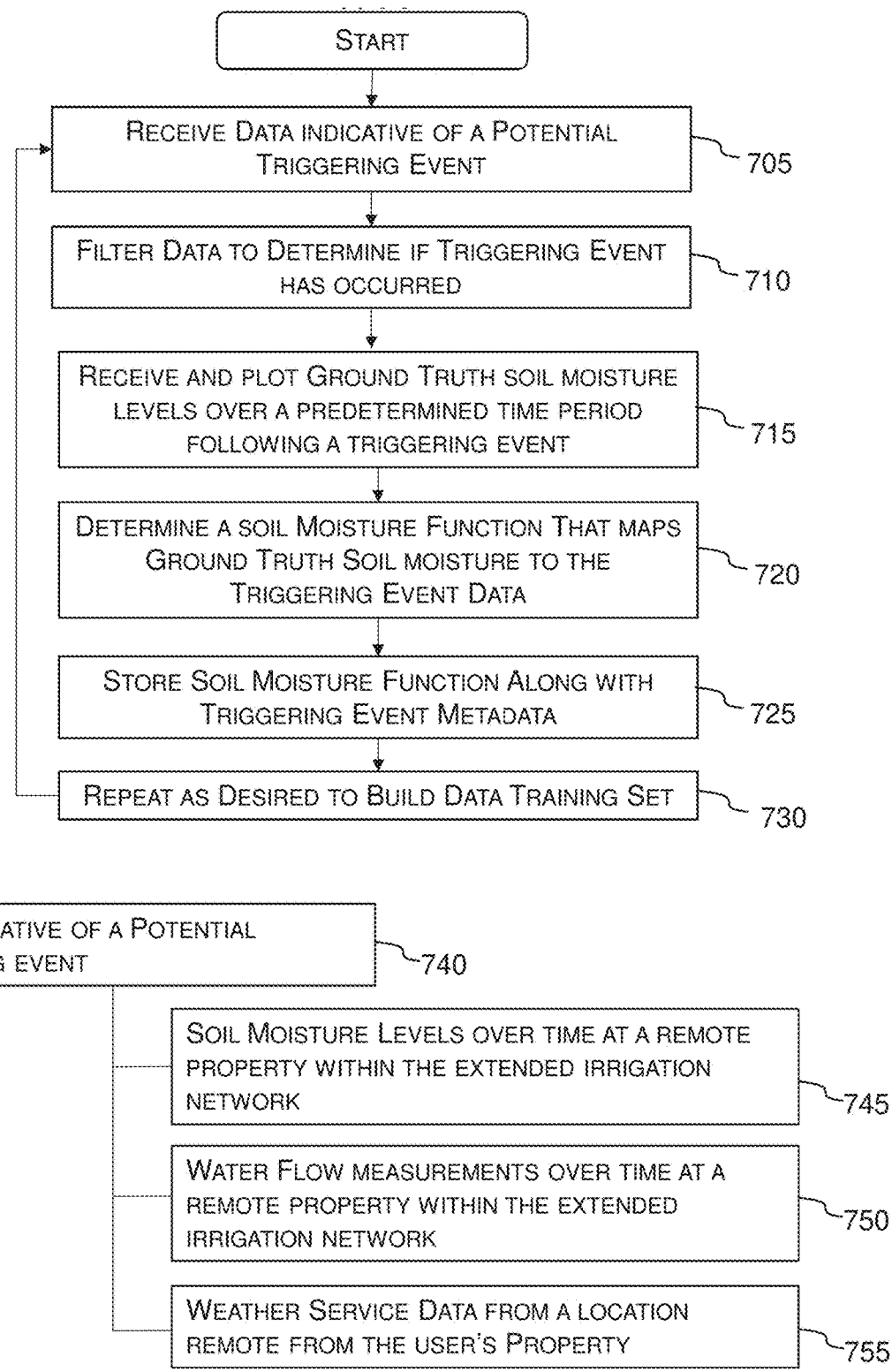
FIG. 7 is an exemplary flow chart illustrating a training data generation process, in accordance with disclosed embodiments.

FIG. 7 is an exemplary flow chart illustrating a training set generation process, in accordance with disclosed embodiments. In some embodiments, model generator 304 may carry out training set process. In step 705, model generator 304 may receive data indicative of a potential triggering event, such as soil moisture levels measured over time at properties in the extended irrigation network, water flow measurements over time at properties in the extended irrigation network, and/or weather service data. Data indicative of a potential triggering event (640 in FIG. 6) may include a measured change in soil moisture levels at a remote property (745), a measured watering event occurring at a remote property (750), a measured precipitation at a remote location such as from weather service data (755), etc.

In step 710, model generator 304 may filter data to determine if a triggering event has occurred, such as by filtering data as described above with respect to FIG. 7. In step 715, model generator 304 may receive and plot the ground truth soil moisture levels over a predetermined time period following the triggering event. For example, 15 minutes, 30 minutes, 60 minutes, 90 minutes, 120 minutes, etc.

In step 720, model generator 304 may determine a soil moisture function that maps ground truth soil moisture levels to the triggering event data. For example, for a precipitation event detected in a city 5 miles away, the model generator may determine that soil moisture increases after a delay or lag time of 10 minutes and generate a soil moisture function to represent the lag time for the ground truth soil moisture level in response to the triggering event. The soil moisture function determined by model generator may also account for the amount of precipitation, for example, the soil moisture function may account for lower ground truth soil moisture levels for a precipitation of 0.2 inches and higher ground truth soil moisture levels for a precipitation of 0.5 inches.

In step 725, model generator 304 may build the training data set by storing the soil moisture function along with model features, such as metadata associated with the triggering event. Model features may represent a variable useful for prediction that may be used in the prediction solution. For example, model features may include the amount of precipitation received within a period, a location associated with the triggering event, a date, a time of day, an air temperature, or a specific property type (such as a property that is uphill/upstream from the client property). In certain embodiments, model generator 304 may store multiple model features and determine a feature importance score for all the stored model features. The feature importance score may reflect the correlation between the selected features and other identified features. For example, model generator 304 may assign a high importance score to a variable or feature that exhibits a high correlation with the other identified features. Alternatively, a feature with low correlation with respect to other features may be assigned a low importance score. Furthermore, in additional or alternative embodiments, the model features may be categorized based in the influence they have in the target result. In some embodiments, the input model features may then be used to determine a model. For example, in a decision tree input model features may be used to make node determinations.

In some embodiments, model generator 304 may score model features using techniques such as Principal Component analysis and/or unsupervised clustering methods. In other embodiments model generator 304 may include line or edge detection, or Digital Signal Processing (DSP) methods. In such embodiments, model generator 304 may implement iterative regressions to evaluate features. For example, model generator 304 may execute algorithms such as least absolute shrinkage and selection operator to determine least squares models for each generated feature to estimate a feature behavior. It will be appreciated that a combination of each of the analyses may be utilized as well.

In some embodiments, training data module 330 may select data based on a specific triggering event detected. For example, prediction system 204 may request a model from model generator 304 for a watering event detected at an adjacent property. Training data module 330 may generate a training data set only using soil moisture functions and ground truth for watering events at the specific adjacent property.

Model generator 304 may generate a candidate model using a training data set. For example, model generator may process the training data set of step 705 to determine coefficients and hyper parameters for a prediction model. The prediction models may be parametric, non-parametric, or semi-parametric. In some embodiments, model generator 304 may create a plurality of decision trees as prediction models. For example, model generator 304 may use a top-down or a bottom-up approach to generate candidate decision trees in step 720. In such embodiments, model generator 304 may generate nodes by finding a discrete function of the input attributes values using a training data set or a training data subset. Based on a splitting metric, a coefficient may be assigned to the node. Decision trees created by model generator 304 may then be used in a random forest analysis.

In other embodiments, model generator 304 may generate neural networks, Group Method of Data Handling (GMDH) algorithms, Naive Bayes classifiers, and/or Multivariate Adaptive Regression Splines. For example, model generator 304 may implement Convolutional Neural Networks (CNN), generating nodes and connections associated with multiple dimensions using the training data. CNNs consist of multiple layers of receptive fields and various combinations of convolutional and fully connected layers. Additionally, model generator 304 may implement Recurrent Neural Networks (RNN), generating nodes and connections with directed cycles that dynamically adjust to behaviors of the training data.

As indicated at step 730, the process may be repeated a plurality of times to generate a plurality of models. In some embodiments, model generator 304 may repeat the process until a minimum of models is generated. For example, prediction system 204 may request that model generator 304 generates models for a random forest analysis. In such embodiments, model generator 304 may generate between 20-100 decision trees to conduct the prediction analysis. Less than 20 models may not provide the required accuracy while more than a 100 decision trees may demand too much computing power. In such embodiments, prediction system may require at least 50 decision trees.

Figure 8A:
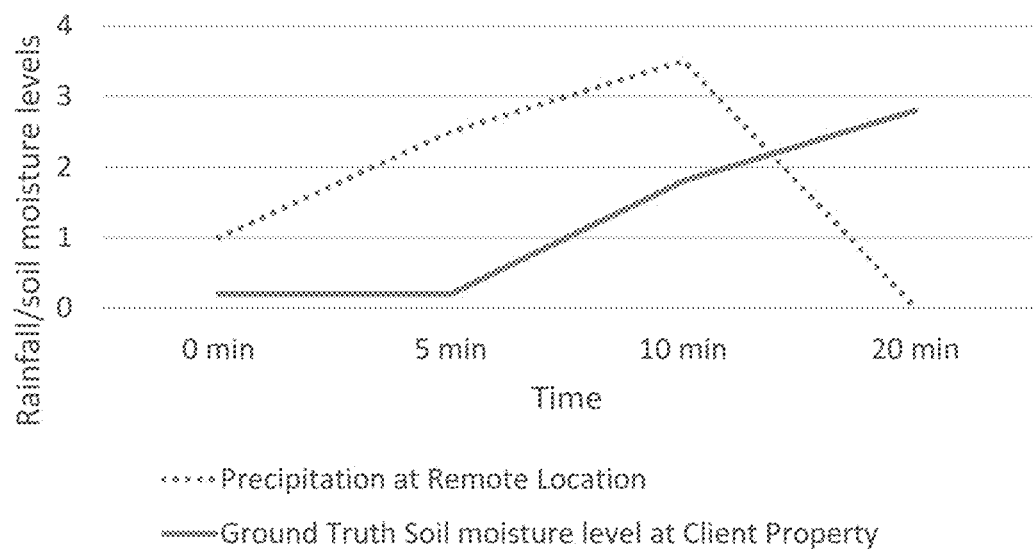
FIG. 8A is an exemplary soil moisture function mapping ground truth soil moisture to a triggering event in accordance with disclosed embodiments.

FIG. 8A is an exemplary predictive soil moisture function, in accordance with disclosed embodiments. In this example, over time, precipitation at a remote location affects the soil moisture levels at the client's property. Here, the precipitation event at the remote location has begun at time value 0. The precipitation event continues at the remote location and the rainfall level increases over time. After a lag time of 5 minutes, the soil moisture levels at the client's property begin to increase. The system could store this as a training function mapping ground truth soil moisture of the client's property as a function of the precipitation triggering event at the remote property. Along with the training function, associated metadata such as the location of the remote property, the time of day of the triggering event, the volume/amount of precipitation of the triggering event, a type for the triggering event (in this case, "precipitation," other types may be events such as a watering event, etc.), a date of the triggering event, etc. may be stored. The system may later retrieve these functions based on the associated metadata to determine the best predictive function for soil moisture of the client's property as a function of the triggering event.

Figure 8B:
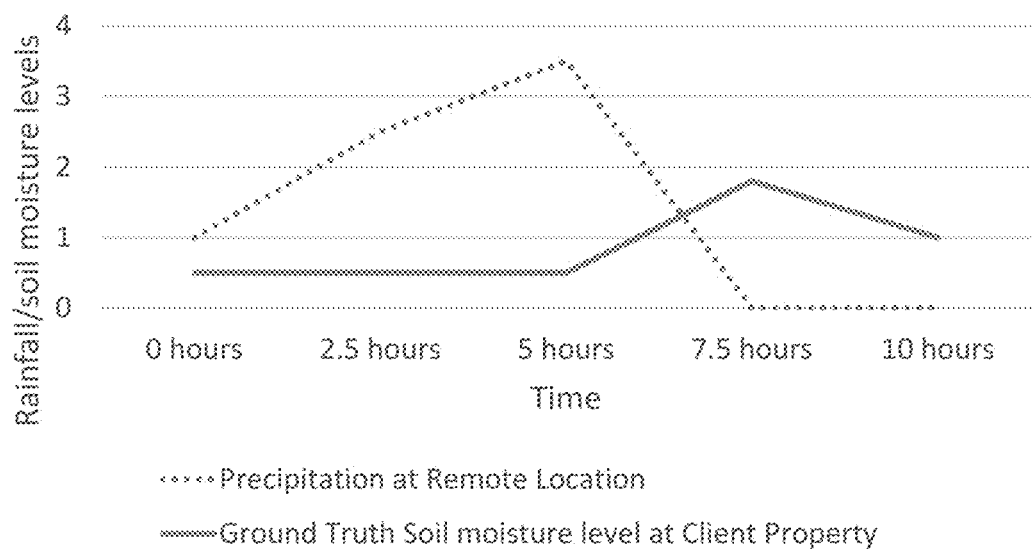
FIG. 8B is another exemplary soil moisture function mapping ground truth soil moisture to a triggering event in accordance with disclosed embodiments.

While FIG. 8A contemplates a lag time of only 5 minutes, it will be appreciated that the lag time could be much longer depending on the location of the remote property associated with the triggering event. For example, the lag time could be a few hours or even a few days. FIG. 8B shows another exemplary predictive soil moisture function, in accordance with disclosed embodiments. Like in FIG. 8A, FIG. 8B shows how over time, precipitation at a remote location affects the soil moisture levels at the client's property. Here, the precipitation event at the remote location has begun at time value 0. The precipitation event continues at the remote location and the rainfall level increases over time. After a lag time of 5 hours, the soil moisture levels at the client's property begin to increase. The system could store this as a training function mapping ground truth soil moisture of the client's property as a function of the precipitation triggering event at the remote property. Along with the training function, associated metadata could be stored.

Figure 8C:
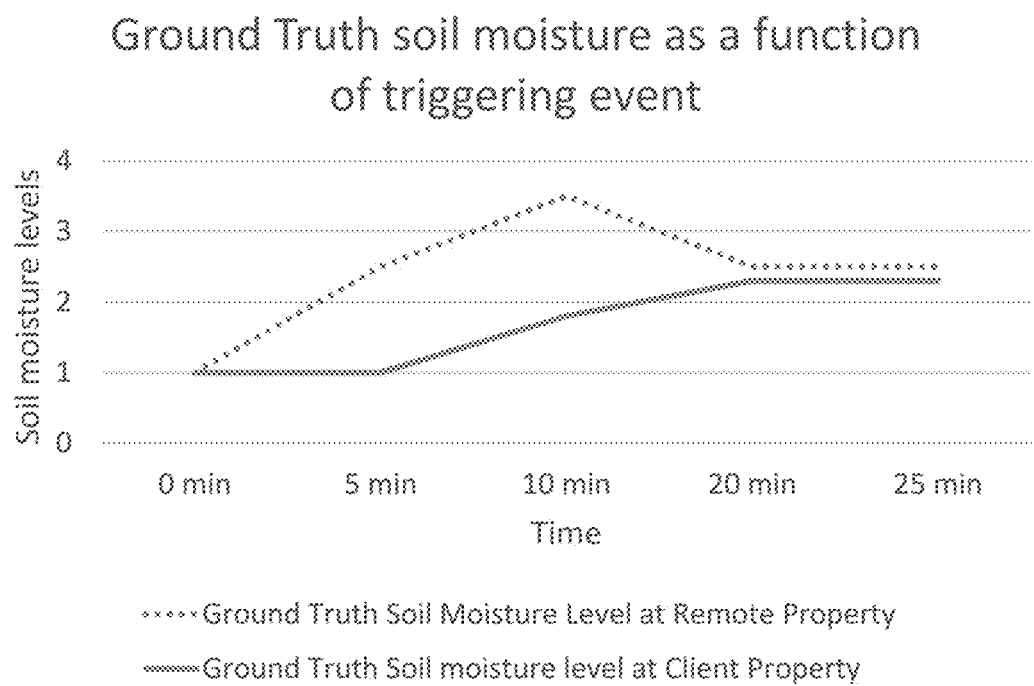
FIG. 8C is another exemplary soil moisture function mapping ground truth soil moisture to a triggering event in accordance with disclosed embodiments.

FIG. 8C is another exemplary predictive soil moisture function, in accordance with disclosed embodiments. In this example, over time, soil moisture levels at a remote location affects the soil moisture levels at the client's property. For example, the remote property could be a property adjacent to the client's property or uphill/upstream from the client's property. Here, the triggering event at the remote location has begun at time value 0. For example, watering at the remote property may begin at time value 0. The watering event continues at the remote property and the soil moisture level increases over time. After a lag time of 5 minutes, the soil moisture levels at the client's property begin to increase. The system could store this as a training function mapping ground truth soil moisture of the client's property as a function of the triggering event at the remote property. Along with the training function, associated metadata may be stored.

Figure 9:
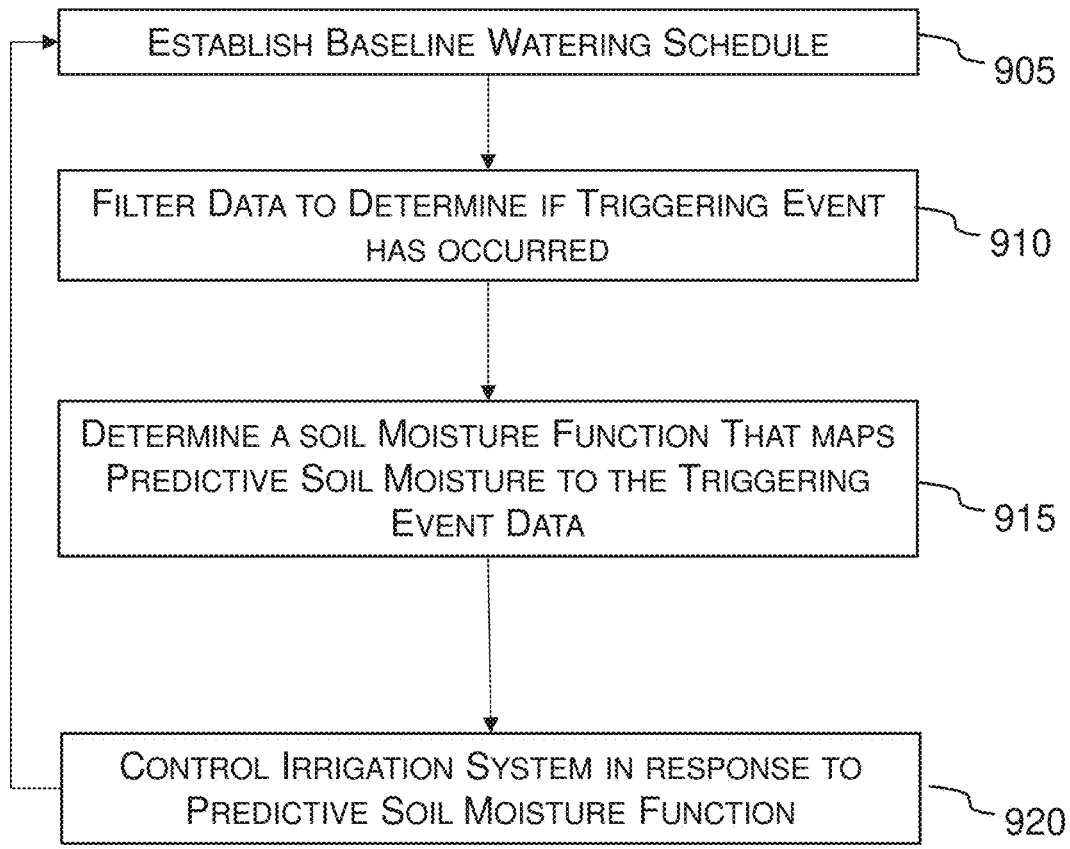
FIG. 9 is an exemplary flow chart illustrating an irrigation control system process.

FIG. 9 is an exemplary flow chart illustrating an overall process that may be taken by an irrigation controller. The irrigation controller may first establish a baseline watering schedule at step 905. This may be done, for example, by analysis of historical watering patterns. Historical weather data from years past that is maintained in weather systems and even local archives may be obtained and utilized to determine the baseline watering schedule. Historical data or other data stored within the system's memory or on database 114 may provide this data to the AI feature. For example a new program water schedule created for spring annual flowers may have been implemented from previous years within specific dates and for specific irrigation amounts and times. The AI feature may recognize from historical data that this was done and would suggest or create a baseline watering schedule that takes into account the spring annual flowers historical watering schedule created in prior years. This may also be applied to other schedule or service appointment such as lawn mowing schedules, and the AI may review prior year's data and make suggestions or auto create appointments or schedules that impact the watering program.

After establishing the baseline watering schedule, the controller may query to determine if the prediction system has detected a triggering event at step 910. For example, the prediction system 204 may gather real-time data relating to onsite rain fall or moisture content in the ground or atmosphere or other environmental features. With this information regarding moisture content or rainfall the system may determine a predictive soil moisture function at step 915, and in response may automatically increase, decrease or otherwise modify the baseline watering schedule and control the irrigation system in response at step 920. This may be done based on the needs of surrounding properties or based on the same inputs from the current property the system is monitoring. One example may include a system that may not have rain sensors, moisture sensors or environmental sensors, while a nearby that property might have any number of these. The AI feature may relay or pull from other property's specific data to make adjustments to the baseline watering schedule at the client's property. This may also allow irrigation customers who may not have all the features of surrounding properties to still take advantage of surrounding property data. For example, as seen in the extended network of irrigation controllers in FIG. 4, property 2 does not have dedicated soil moisture sensors nor water flow detectors. Property 3 and/or property 1 may provide ground truth data for property 2.

Although the description herein is explained with reference to a client communicating device such as a smart device, the described methods may also be implemented in any other devices, as will be understood by those skilled in the art. For a firmware, and/or software implementation, the methodologies can be implemented with modules (e.g., procedures, functions, and so on) that perform the functions described herein. Any machine readable medium tangibly embodying instructions can be used in implementing the methodologies described herein. For example, software codes and programs can be stored in a memory and executed by a processing unit. Memory can be implemented within the processing unit or may be external to the processing unit. As used herein the term "memory" refers to any type of long term, short term, volatile, nonvolatile, or other storage devices and is not to be limited to any particular type of memory or number of memories, or type of media upon which memory is stored.

The irrigation system 100 described herein (FIG. 1), can be implemented in any network environment comprising a variety of network devices, including routers, bridges, servers, computing devices, storage devices, etc. The communication network, and the various devices therein, may contain other devices, systems and/or media not specifically described above. For example, in one implementation it is anticipated that the system 100 may be implemented on an application server or web server. In such a configuration, a client device 104 may communicate instructions to an application or web server, and/or receive input from an application or web server. The application or web server may communicate instructions to hardware 108, such as a sprinklers 112 to control such hardware in response to the predicted soil moisture level from the moisture content prediction system and communicated to the hardware 108 (described in additional detail below with reference to FIG. 3). In another configuration, the system 100 may include not just an application or web server, but the system may also comprise hardware to be controlled by the system, such as one or more watering devices, etc. (see block diagram of system 100 in FIG. 2). It will be appreciated that various aspects of the system may be implemented either by including the hardware to be controlled within the system, or by communication of a signal to the hardware to be controlled outside the system by a network 106.

A system for predicting soil moisture at a first property based on a triggering event, and managing an irrigation system at the first property in response to the triggering event the system may comprise: a processor in communication with a prediction system and a database; and a storage medium storing instructions that, when executed, configure the processor to: establish a baseline watering schedule comprising one or more baseline watering events; receive at least one of real-time weather data, real-time water flow data, and real-time soil moisture data; filter the at least one of weather data, water flow data, and soil moisture data to determine if a potential triggering event has occurred; where a potential triggering event has occurred, comparing at least one feature of the potential triggering event to at least one model feature of stored historical triggering event models to determine a correlation value between the potential triggering event and stored historical triggering events, the model features including at least one of type, location, date, time, and amount; where the correlation value is above a predetermined threshold, making a soil moisture prediction for the first property based on at least one stored historical triggering event model; and where soil moisture prediction for the first property will increase within a predetermined amount of time of a baseline watering event, delaying the baseline watering event.

In some configurations, the soil moisture function comprises a stored soil moisture function mapping ground truth soil moisture data to the stored historical triggering event. The system may further comprise the storage medium storing instructions that, when executed, configure the processor to build a training set, the training set comprising soil moisture functions for the first property that map predictive soil moisture at the first property to at least one of real-time weather data, real-time water flow data, and real-time soil moisture data taken at a location remote from the property.

The instructions that configure the processor to build the training set may comprise instructions that configure the processor to: receive at least one of weather data, water flow data, and soil moisture data taken at a location remote from the first property; filter the at least one of weather data, water flow data, and soil moisture data to determine if a potential triggering event has occurred; receive a ground truth soil moisture level at the property over a predetermined time period following the potential triggering event; determine a soil moisture function that maps predictive soil moisture to the at least one of weather data, water flow data, and soil moisture data over the predetermined time period following the potential triggering event; when the soil moisture function maps an increase in predictive soil moisture, tag the potential triggering event as a historical triggering event; and store the historical triggering event and the soil moisture function with its metadata, the metadata comprising at least one of: a type, a location, a lag time, and an amount.

A model feature of stored historical triggering event models may include at least one of a type of the triggering event, a location of the triggering event, and an amount of the triggering event. A type of triggering event may include at least one of a soil moisture change over time at the second property, a water flow measurement change over time at the second property, and weather service data from a location remote from the first property.

A feature of the potential triggering event may include at least one of a type of the potential triggering event, a location of the potential triggering event, and an amount of the potential triggering event.

According to another aspect, a system is disclosed for predicting soil moisture at a first property based on a triggering event, and managing an irrigation system at the first property in response to the triggering event, the system comprising: a processor in communication with a prediction system and a database; and a storage medium storing instructions that, when executed, configure the processor to: establish a baseline watering schedule comprising one or more baseline watering events; receive data associated with a potential triggering event at a second property, comparing at least one characteristic of the potential triggering event to at least one characteristic of stored historical triggering events to determine a correlation value between the potential triggering event and stored historical triggering events, the stored historical triggering events comprising metadata including at least one of location of the stored historical triggering event, and an amount of the stored historical triggering event; where the correlation value is above a predetermined threshold, generating a soil moisture prediction model for the first property based on a soil moisture function of at least one stored historical triggering event; and where soil moisture prediction for the first property will increase within a predetermined amount of time of a baseline watering event, delaying the baseline watering event.

The instructions may further configure the processor to: determine a soil moisture level prediction model for the triggering event based on ground truth soil moisture levels over a predetermined timeframe; generate a training data set based on the triggering event and soil moisture level prediction model; and communicate the soil moisture level prediction model for the triggering event to the prediction system.

A system is also disclosed for predicting soil moisture at a first property based on a precipitation event at a location remote from the first property, and managing an irrigation system at the first property in response to the precipitation event at the location remote from the first property, the system comprising: a processor in communication with a prediction system and a database; and a storage medium storing instructions that, when executed, configure the processor to: establish a baseline watering schedule comprising one or more baseline watering events; receive real-time weather data for the location remote from the first property; filter the real-time weather data for the location remote from the first property to determine if the precipitation event has occurred; where the precipitation event has occurred, generating a predictive soil moisture model based on at least one stored historical precipitation event models, the at least one stored historical precipitation event model comprising model features; and modifying the baseline watering schedule in response to the predictive soil moisture model.

In some configurations, the processor may determine an accuracy of the predictive soil moisture model based on ground truth soil moisture levels. The precipitation event may further comprise features, the features comprises at least one of a location of the precipitation event, a date of the precipitation event, a time of the precipitation event, and an amount of the precipitation event. Similarly, the model features may comprise at least one of a location of the historical precipitation event, a date of the historical precipitation event, a time of the historical precipitation event, and an amount of the historical precipitation event.

Although the foregoing disclosure provides many specifics, these should not be construed as limiting the scope any of the ensuing claims. Other embodiments may be devised which do not depart from the scopes of the claims. Features from different embodiments may be employed separately or in combination. Accordingly, all additions, deletions and modifications to the disclosed subject matter that fall within the scopes of the claims are to be embraced thereby. The scope of each claim is indicated and limited only by its plain language and the full scope of available legal equivalents to its elements.

I claim:

1. A system for predicting soil moisture at a first property based on a triggering event, and managing an irrigation system at the first property in response to the triggering event the system comprising:
   a processor in communication with a prediction system and a database; and
   a storage medium storing instructions that, when executed, configure the processor to:
   establish a baseline watering schedule comprising one or more baseline watering events;
   receive at least one of real-time weather data, real-time water flow data, and real-time soil moisture data;
   filter the at least one of real-time weather data, real-time water flow data, and real-time soil moisture data to determine if a potential triggering event has occurred;
   where the potential triggering event has occurred, comparing at least one feature of the potential triggering event to at least one model feature of stored historical triggering event models to determine a correlation value between the potential triggering event and stored historical triggering events, the at least one model feature including at least one of type, location, date, time, and amount;
   where the correlation value is above a predetermined threshold, making a soil moisture prediction for the first property based on the at least one stored historical triggering event model; and
   where soil moisture prediction for the first property will increase within a predetermined amount of time of a baseline watering event, delaying the baseline watering event.

2. The system of claim 1, wherein the soil moisture prediction comprises a stored soil moisture function mapping ground truth soil moisture data to the stored historical triggering event models.

3. The system of claim 1, further comprising the storage medium storing instructions that, when executed, configure the processor to build a training set, the training set comprising soil moisture functions for the first property that map predictive soil moisture at the first property to at least one of real-time weather data, real-time water flow data, and real-time soil moisture data taken at a location remote from the first property.

4. The system of claim 3, wherein the instructions that configure the processor to build the training set comprise instructions that configure the processor to: receive at least one of weather data, water flow data, and soil moisture data taken at a location remote from the first property; filter the at least one of weather data, water flow data, and soil moisture data to determine if the potential triggering event has occurred; receive a ground truth soil moisture level at the property over a predetermined time period following the potential triggering event; determine a soil moisture function that maps predictive soil moisture to the at least one of weather data, water flow data, and soil moisture data over the predetermined time period following the potential triggering event; when the soil moisture function maps an increase in predictive soil moisture, tag the potential triggering event as a historical triggering event; and store the historical triggering event and the soil moisture function with its metadata, the metadata comprising at least one of: a type, a location, a lag time, and an amount.

5. The system of claim 1, wherein at least one model feature of stored historical triggering event models comprises at least one of a type of the triggering event, a location of the triggering event, and an amount of the triggering event.

6. The system of claim 5, wherein a type of triggering event comprises at least one of a soil moisture change over time at a second property, a water flow measurement change over time at the second property, and weather service data from a location remote from the first property.

7. The system of claim 1, wherein at least one feature of the potential triggering event comprises at least one of a type of the potential triggering event, a location of the potential triggering event, and an amount of the potential triggering event.

8. The system of claim 1, wherein the processor configured to filter the at least one of weather data, water flow data, and soil moisture to determine if a potential triggering event has occurred comprises the processor filtering the at least one of weather data, water flow data, and soil moisture based on at least one of location, type, and amount.

9. The system of claim 1, wherein the system further comprises at least one soil moisture sensor in communication with the processor, and wherein the processor is further configured to receive ground truth soil moisture data from the at least one soil moisture sensor, and compare the soil moisture prediction to the ground truth soil moisture data.

10. The system of claim 9, wherein when the processor is further configured to activate the baseline watering event after a predetermined amount of time if the ground truth soil moisture data is lower than the soil moisture prediction.

11. A system for predicting soil moisture at a first property based on a triggering event, and managing an irrigation system at the first property in response to the triggering event, the system comprising:
  a processor in communication with a prediction system and a database; and
  a storage medium storing instructions that, when executed, configure the processor to:
  establish a baseline watering schedule comprising one or more baseline watering events;
  receive data associated with a potential triggering event at a second property, comparing at least one characteristic of the potential triggering event to at least one characteristic of stored historical triggering events to determine a correlation value between the potential triggering event and stored historical triggering events, the stored historical triggering events comprising metadata including at least one of location of the stored historical triggering event, and an amount of the stored historical triggering event;
  where the correlation value is above a predetermined threshold, generating a soil moisture prediction model for the first property based on a soil moisture function of at least one stored historical triggering event; and
  where soil moisture prediction for the first property will increase within a predetermined amount of time of a baseline watering event, delaying the baseline watering event.

12. The system of claim 11 wherein the instructions further configure the processor to:
  determine a soil moisture level prediction model for the triggering event based on ground truth soil moisture levels over a predetermined timeframe;
  generate a training data set based on the triggering event and soil moisture level prediction model; and
  communicate the soil moisture level prediction model for the triggering event to the prediction system.

13. The system of claim 11, wherein the system predicts soil moisture at a first property based on a triggering event at a second property, the system further comprising:
  a network;
  a first irrigation controller for controlling irrigation at the first property, the first irrigation controller in communication with the processor and the network;
  a second irrigation controller for controlling irrigation at the second property, the second irrigation controller in communication with a second processor and the network;
  a first soil moisture sensor at the first property in communication with the first irrigation controller; and
  a second soil moisture sensor at the second property in communication with the second irrigation controller.

14. A system for predicting soil moisture at a first property based on a precipitation event at a location remote from the first property, and managing an irrigation system at the first property in response to the precipitation event at the location remote from the first property, the system comprising:
  a processor in communication with a prediction system and a database; and
  a storage medium storing instructions that, when executed, configure the processor to:
  establish a baseline watering schedule comprising one or more baseline watering events;
  receive real-time weather data for the location remote from the first property;
  filter the real-time weather data for the location remote from the first property to determine if the precipitation event has occurred;
  where the precipitation event has occurred, generating a predictive soil moisture model based on at least one stored historical precipitation event model, the at least one stored historical precipitation event model comprising model features; and
  modifying the baseline watering schedule in response to the predictive soil moisture model.

15. The system of claim 14, wherein the instructions, when executed, further configure the processor to determine an accuracy of the predictive soil moisture model based on ground truth soil moisture levels.

16. The system of claim 15, wherein the precipitation event further comprises features, the features comprises at least one of a location of the precipitation event, a date of the precipitation event, a time of the precipitation event, and an amount of the precipitation event.

17. The system of claim 16, wherein the model features comprise at least one of a location of the stored historical precipitation event, a date of the historical precipitation event, a time of the historical precipitation event, and an amount of the historical precipitation event.

* * * * *